US008226537B2

(12) United States Patent
Pittinger et al.

(10) Patent No.: US 8,226,537 B2
(45) Date of Patent: Jul. 24, 2012

(54) BLOOD PROCESSING APPARATUS WITH CELL SEPARATION CHAMBER WITH BAFFLES

(75) Inventors: John Pittinger, Evergreen, CO (US); Robert Langley, Westminster, CO (US); Mary Langley, legal representative, Westminster, CO (US); Logan Fender, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 13/111,039

(22) Filed: May 19, 2011

(65) Prior Publication Data

US 2011/0224064 A1 Sep. 15, 2011

Related U.S. Application Data

(62) Division of application No. 12/209,793, filed on Sep. 12, 2008, now Pat. No. 7,963,901.

(51) Int. Cl.
*B04B 7/12* (2006.01)
(52) U.S. Cl. .......................... 494/45; 494/67
(58) Field of Classification Search .......... 494/45, 494/67, 74, 76–80; 604/4.01–6.16; 210/782
See application file for complete search history.

(56) References Cited

U.S. PATENT DOCUMENTS

| | | | |
|---|---|---|---|
| 2,616,619 A | 11/1952 | MacLeod | |
| 3,391,597 A | 7/1968 | Gropper | |
| 5,405,308 A | 4/1995 | Headley et al. | |
| 5,674,173 A | 10/1997 | Hlavinka et al. | |
| 5,722,926 A | 3/1998 | Hlavinka et al. | |
| 5,906,570 A | 5/1999 | Langley et al. | |
| 5,939,319 A | 8/1999 | Hlavinka et al. | |
| 5,951,877 A | 9/1999 | Langley et al. | |
| 6,051,146 A | 4/2000 | Green et al. | |
| 6,053,856 A | 4/2000 | Hlavinka | |
| 6,334,842 B1 | 1/2002 | Hlavinka et al. | |
| 6,354,986 B1 | 3/2002 | Hlavinka et al. | |
| 7,201,848 B2 | 4/2007 | Antwiler et al. | |
| 7,422,693 B2 | 9/2008 | Carter et al. | |
| 7,549,956 B2 | 6/2009 | Hlavinka et al. | |
| 7,963,901 B2 | 6/2011 | Langley et al. | |
| 2006/0147895 A1* | 7/2006 | Purdum | 435/2 |

FOREIGN PATENT DOCUMENTS

DE 2658926 A1 6/1978
(Continued)

OTHER PUBLICATIONS

Figdor, Carl G. et al., "Theory and Practice of Centrifugal Elutriation (CE) Factors Influencing the Separation of Human Blood Cells", Cell Biophysics, 1983, vol. 5, pp. 105-118.

(Continued)

*Primary Examiner* — Walter D Griffin
*Assistant Examiner* — Timothy Cleveland
(74) *Attorney, Agent, or Firm* — John R. Merkling

(57) ABSTRACT

A disposable blood separation set of a centrifugal blood processing system comprising a blood processing chamber adapted to be mounted on a rotor of a centrifuge; a frustro-conical cell separation chamber in fluid communication with the processing chamber, the cell separation chamber a baffle within a separation area. The baffle may have a plurality of vanes with openings therein. A protruding inlet may have a frustro-conical inner surface that slants radially outwardly from an inlet to a mouth of the protruding inlet. A circumferential well may surround the protruding inlet.

10 Claims, 6 Drawing Sheets

FOREIGN PATENT DOCUMENTS

| | | |
|---|---|---|
| DE | 3700122 A1 | 7/1988 |
| DE | 3734170 A1 | 4/1989 |
| EP | 0406485 A1 | 1/1991 |
| EP | 0408462 B1 | 1/1991 |
| WO | 94/06535 A1 | 3/1994 |
| WO | 96/33206 A1 | 10/1996 |

OTHER PUBLICATIONS

Grabske, Robert J., "Separating Cell Populations by Elutriation", Beckman Instruments Inc., 1978, pp. 1-8.

Lutz, M.P. et al., "Large-Scale Cell Separation by Centrifugal Elutriation", Analytical Biochemistry, 1992, vol. 200, pp. 376-380.

Tulp, A. and Barnhoorn, M.G., "A Separation Chamber to Sort Cells and Cell Organelles by Weak Forces. V.A. Sector Shaped Chamber and It's Application to the Separation of Peripheral Blood Cells", Journal of Immunological Methods, 1984, vol. 69, pp. 281-295.

Sanderson, Richard J. et al., "Design Principles for a Counterflow Centrifugation Cell Separation Chamber", Analytical Biochemistry, 1976, vol. 71, pp. 615-622.

PCT/US2009/037609: "International Search Report and Written Opinion", mailed Aug. 13, 2009.

* cited by examiner

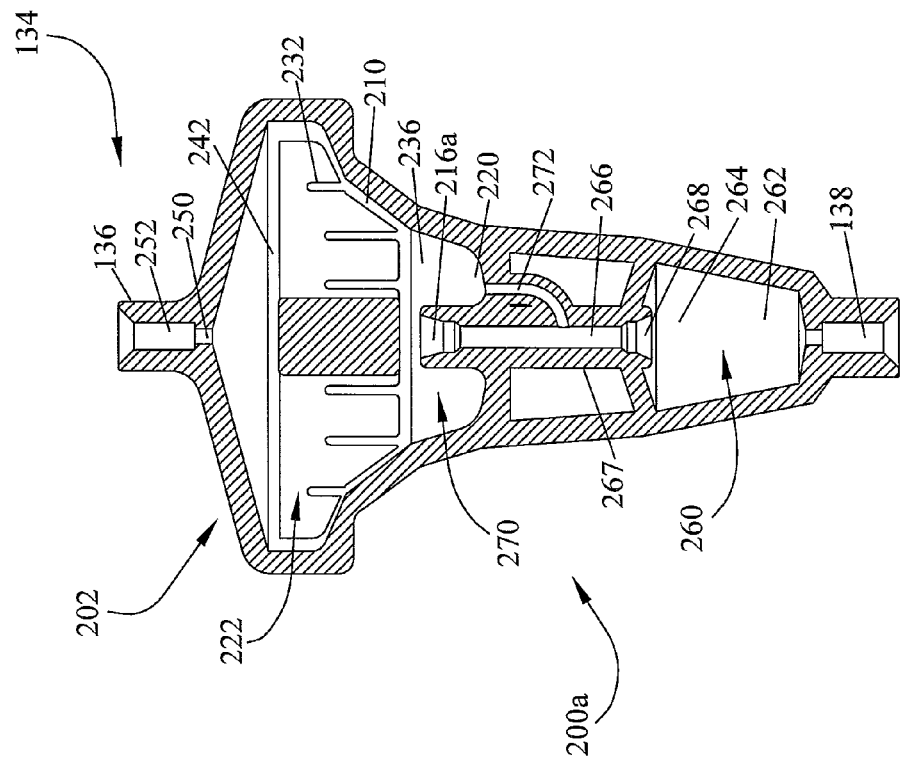
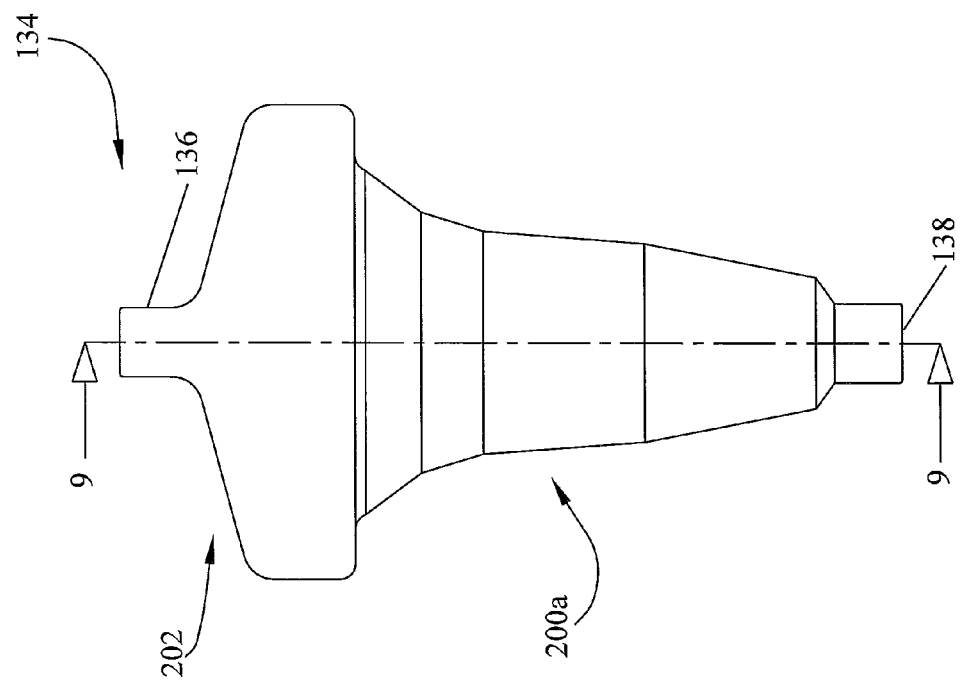
Figure 9
Figure 8

BLOOD PROCESSING APPARATUS WITH CELL SEPARATION CHAMBER WITH BAFFLES

CROSS REFERENCE TO RELATED APPLICATIONS

This application is a divisional of U.S. Utility application Ser. No.: 12/209,793, filed Sep. 12, 2008, now U.S. Pat. No. 7,963,901.

BACKGROUND OF THE INVENTION

1. Field of the Invention

The present invention relates to an apparatus and method for separating particles or components of a biologic fluid, such as blood. The invention has particular advantages in connection with separating blood components, such as white blood cells and platelets.

2. Description of the Related Art

In many different fields, liquids carrying particles must be filtered or processed to obtain either a purified liquid or purified particle end product. In its broadest sense, a filter is any device capable of removing or separating particles from a substance. Thus, the term "filter" as used herein is not limited to a porous media material but includes many different types of devices and processes where particles are either separated from one another or from liquid.

In the medical field, it is often necessary to filter blood. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets. Most current purification devices rely on density and size differences or surface chemistry characteristics to separate and/or filter the blood components.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating at a very rapid speed and centrifugal force stratifies the blood components, so that particular components may be separately removed. Components are removed through ports arranged within stratified layers of blood components.

White blood cells and platelets in plasma form a medium-density, stratified layer or "buffy coat". Because typical centrifuge collection processes are unable to consistently and satisfactorily separate white blood cells from platelets in the buffy coat, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5-20% of the platelets. These conventional filters may also reduce "platelet viability", meaning that once the platelets pass through a filter, a percentage of the platelets cease to function properly and may be partially or fully inactivated. In addition, porous filters may cause the release of bradykinin, an inflammation mediator and vasodialator, which may lead to hypotensive episodes in a patient. Porous filters are also expensive and often require additional time-consuming manual labor to perform a filtration process. Although porous filters are effective in removing a substantial number of white blood cells, inactivated platelets may clog the filter. Therefore, the use of at least some porous filters is not feasible in on-line processes.

Another separation process is one known as centrifugal elutriation. This process separates cells suspended in plasma without the use of a membrane filter. The plasma, which carries the cells in suspension, is introduced into a funnel-shaped chamber located on a spinning centrifuge. As additional liquid flows through the chamber, it sweeps smaller sized, slower-sedimenting cells toward an elutriation boundary within the chamber, while larger, faster-sedimenting cells migrate to an area of the chamber having the greatest centrifugal force. This type of chamber, called a leuko-reduction or LRS chamber, is described, for example, in U.S. Pat. Nos. 5,674,173 and 6,053,856. It is desirable for an LRS chamber to separate greater than 99.99% of entrained WBC from platelet or plasma products obtained by centrifugal apheresis, which is an extremely high value. The process for cell separation employs a saturated bed that operates in the dense-phase flow regime, which is characterized by high cell density and relatively low fluid flow rate. The primary phenomena that limit LRS performance are Coriolis effects and laminar mixing. Both effects disrupt the desired ideal uniform axial flow in the chamber and the effects have not been completely eliminated in prior configurations.

For these and other reasons, there is a need to improve separation of components of blood in centrifugal blood separators.

SUMMARY OF THE INVENTION

The present invention comprises a centrifuge for separating particles suspended in a fluid, particularly blood and blood components. The apparatus has a blood processing vessel mounted on a rotor of a centrifuge. The elutriation chamber described herein both filters white blood cells from a separated blood component comprising plasma, platelets and white blood cells and suspends the white cells within the elutriation chamber for return to the donor. The flow of fluid into the chamber is separated from the chamber walls by a protruding inlet that extends into the chamber. Laminar mixing of the fluid is restrained by the vanes of a baffle. In addition, a recirculation channel may normalize particle flow rate into the chamber and may return white blood cells to suspension within the chamber or to the donor, according to the steps of the blood collection procedure. Successive chambers may provide staged filtration of the white blood cells from the blood components passing through the elutriation apparatus.

It is an object of the present invention to provide a disposable blood separation set comprising a blood processing chamber adapted to be mounted on a rotor of a centrifuge;

a rigid, generally frustro-conical cell separation chamber in fluid communication with the processing chamber; the cell separation chamber having a protruding inlet in the cell separation chamber, the protruding inlet extending into the separation area and being spaced away from the inner wall. Further, the protruding inlet may have a generally frustro-conical inner surface that slants radially outwardly from an inlet to a mouth of the protruding inlet. A circumferential well may surround the protruding inlet.

Another object of the invention is to provide a cell separation chamber with a baffle within a separation area. The baffle may have a plurality of vanes with openings therein.

A further object is to provide a disposable blood separation set having a protruding inlet and a baffle in a separation chamber wherein the baffle has a bottom edge, spaced away from the protruding inlet. The baffle may also have an upper edge spaced away from an outlet.

It is also an object of the invention to provide a disposable blood separation set having a recirculation channel fluidly coupling a well surrounding a protruding inlet to an inlet connected to the protruding inlet.

Another object is to provide a disposable blood separation set comprising an initial separation area having a generally frustro-conical shape and being in fluid communication with an inlet, a second separation area having a generally frustro-conical shape and being in fluid communication with an outlet, and a tube fluidly connecting the initial separation area and the second separation area.

It is to be understood that both the foregoing general description and the following detailed description are exemplary, and are intended to provide further explanation of the invention as claimed.

BRIEF DESCRIPTION OF THE DRAWINGS

FIG. 8 is a plan view of a second embodiment of the cell separation chamber.

FIG. 9 is a cross sectional view of the cell separation chamber of FIG. 8, taken along line 9-9.

DETAILED DESCRIPTION

Figure 1:
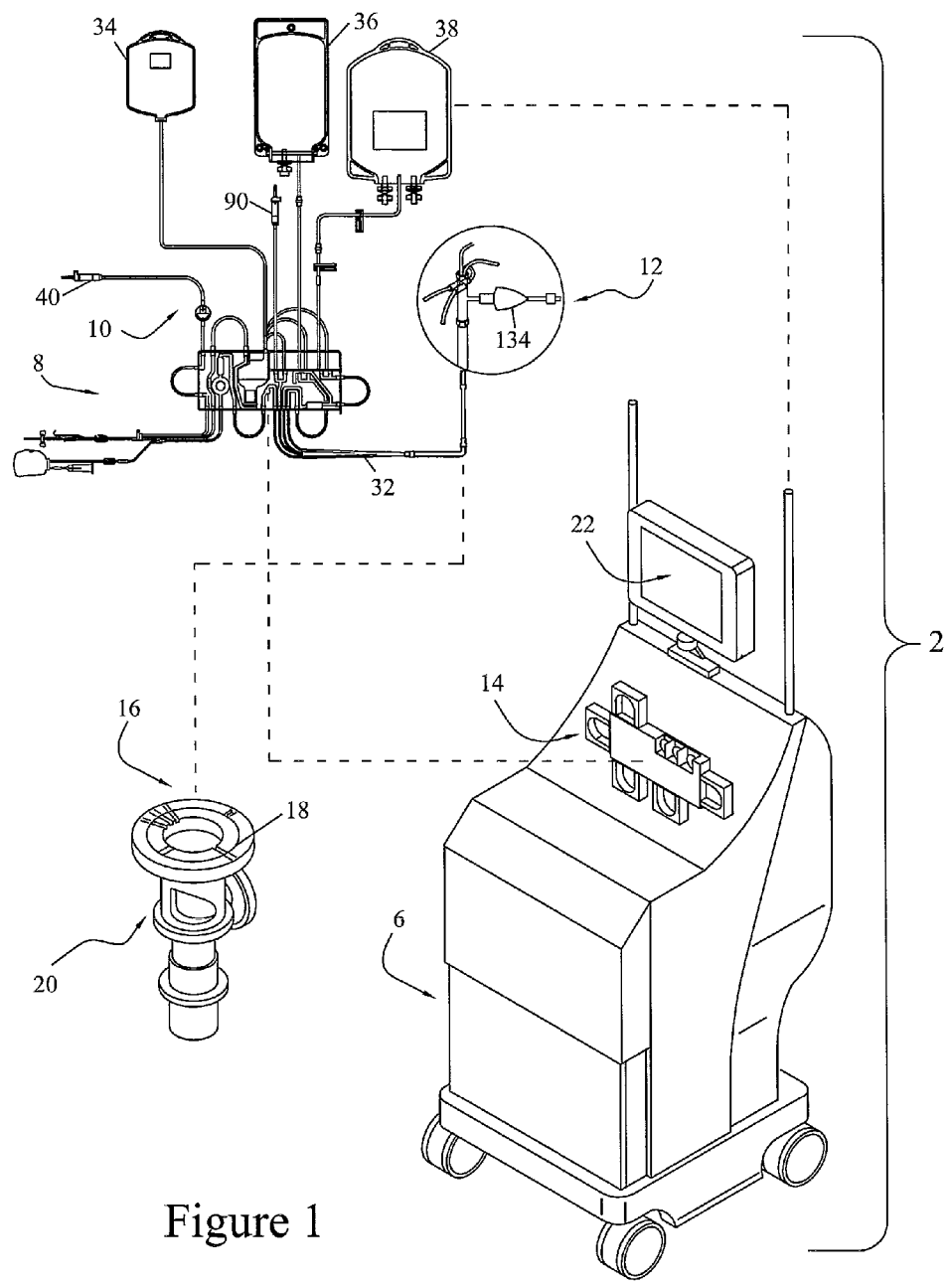
FIG. 1 is a schematic view of one embodiment of an apheresis system, which can be used in or with the present invention.

To describe the present invention, reference will now be made to the accompanying drawings. The present invention may be used with a blood processing apparatus such as a TRIMA® or TRIMA ACCEL® blood component centrifuge manufactured by CaridianBCT, Inc. The invention may also be used with other blood component centrifuges. The Trima or Trima Accel centrifuges incorporate a one-omega/two-omega seal-less tubing connection as disclosed in U.S. Pat. No. 4,425,112 to Ito, and as know in the art to provide a continuous flow of blood to and from the rotor of an operating centrifuge without requiring a rotating seal.

The present invention comprises an improved leuko-reduction ("LRS") chamber for removal of white blood cells ("WBC") from blood components. It is desirable for an LRS chamber to separate greater than 99.99% of entrained WBC from platelet or plasma products obtained by centrifugal apheresis, which is an extremely high value. The process for this separation is based on the phenomenon of particle sedimentation in a fluid. The separated WBC consist of about 95% mononuclear cells (which are about 90% leukocytes and 10% monocytes) and about 5% granulocytes. To accommodate the apheresis collection process, the LRS chamber functions in an automatic mode as a continuous-feed process, which requires an overflowing saturated bed of platelets above a bed of mononuclear cells, which continuously accumulate during the collection. The saturated bed requirement operates in the dense-phase flow regime, which is characterized by high cell density. The primary phenomena that limit LRS performance are Coriolis effects and the laminar mixing that inevitably occurs in a low-velocity situation that is unconstrained by physical boundaries. Both effects disrupt the desired ideal uniform axial flow in the chamber, overcoming to some extent the axial sedimentation forces that separate WBC from platelets. The improved LRS chamber described herein comprises an extended or protruding inlet port and chamber flow baffles. Coriolis effects are reduced by the extended inlet port, and laminar mixing is reduced by flow baffles.

The protruding inlet port is a tube that transfers the entering flow past a critical area where the wall of the chamber forms the apex of a cone opening into the body of the chamber. The function of the protruding port is to virtually eliminate a flow path along the wall that is caused by Coriolis acceleration. Coriolis acceleration pushes fluid entering the chamber towards the leading chamber wall. This entering fluid contains high concentrations of WBC. If the fluid is pushed against the wall, rather than remaining generally in the center of the chamber, the fluid tends to flow up the wall, circumventing the bed of white blood cells and platelets that captures WBC in the chamber by sedimentation forces. This has always been, and still is, a problem for elutriation technology, and for LRS technology in particular. The magnitude of Coriolis acceleration is proportional to the radial flow velocity, and the chamber wall that the entering flow is directed to provides a boundary layer flow path with reduced flow resistance. The protruding inlet port functions, first, by having an exit diameter much larger than the internal diameter of the collect tubing entrance, thereby drastically reducing the flow velocity as it exits the port into the chamber; second, by conveying the entering flow to a point inside the chamber far removed from the chamber wall and close to where the low-velocity cell bed sets up; and, third, by creating a rapid diffusion and dissipation of the cell-carrying flow momentum into the relatively quiescent cell bed, thereby virtually eliminating Coriolis effects.

The thin-wall flow baffles provide the physical boundaries that constrain the development and growth of random non-uniform laminar flows that cause undesirable mixing in the chamber. The six-vane baffle design divides the bulk of the chamber volume into six smaller compartments. The vanes have small openings along most of their length in order to allow low-magnitude flow/pressure variations to communicate and equilibrate among the six compartments, thus preventing any significant undesirable unequal flows, or channeling of fluid through the fluidized bed. The openings can be open-ended slots to facilitate molding of the parts. The baffles stop short of the major diameter of the chamber, providing a volume that serves as a flow-equalizing plenum prior to a uniform flow entering the exit cone.

A preferred blood apheresis system 2 for use with the present invention is schematically illustrated in FIG. 1. System 2 provides for a continuous blood component separation process. Generally, whole blood is withdrawn from a donor and is substantially continuously provided to a blood component separation device 6 where the blood is separated into various components and at least one of these blood components is collected from the device 6. One or more of the separated blood components may be either collected for subsequent use or returned to the donor. In the blood apheresis system 2, blood is withdrawn from the donor and directed through a bag and tubing set 8, which includes an extracorporeal tubing circuit 10, and a blood processing vessel 12, which together define a closed, sterile and disposable system. The set 8 is adapted to be mounted in the blood component separation device 6. The separation device 6 includes a pump/valve/sensor assembly 14, which interfaces with the extracorporeal tubing circuit 10, and a centrifuge assembly 16, which interfaces with the blood processing vessel 12.

The centrifuge assembly 16 may include a channel 18 in a rotatable rotor assembly 20, which provides the centrifugal forces required to separate blood into its various blood component types by centrifugation. The blood processing vessel 12 may then be fitted within the channel 18. Blood can flow substantially continuously from the donor, through the extracorporeal tubing circuit 10, and into the rotating blood processing vessel 12. Within the blood processing vessel 12, blood may be separated into various blood component types and at least one of these blood component types (e.g., white blood cells, platelets, plasma, or red blood cells) may be removed from the blood processing vessel 12. Blood components that are not being retained for collection or for therapeutic treatment (e.g., platelets and/or plasma) are also removed from the blood processing vessel 12 and returned to the donor via the extracorporeal tubing circuit 10. Various alternative apheresis systems (not shown) may also make use of the present invention, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 6 is controlled by one or more processors included therein, and may advantageously comprise a plurality of embedded computer processors to accommodate interface with ever-increasing PC user facilities (e.g., CD ROM, modem, audio, networking and other capabilities). In order to assist the operator of the apheresis system 2 with various aspects of its operation, the blood component separation device 6 includes a graphical interface 22 with an interactive touch screen.

Figure 2:
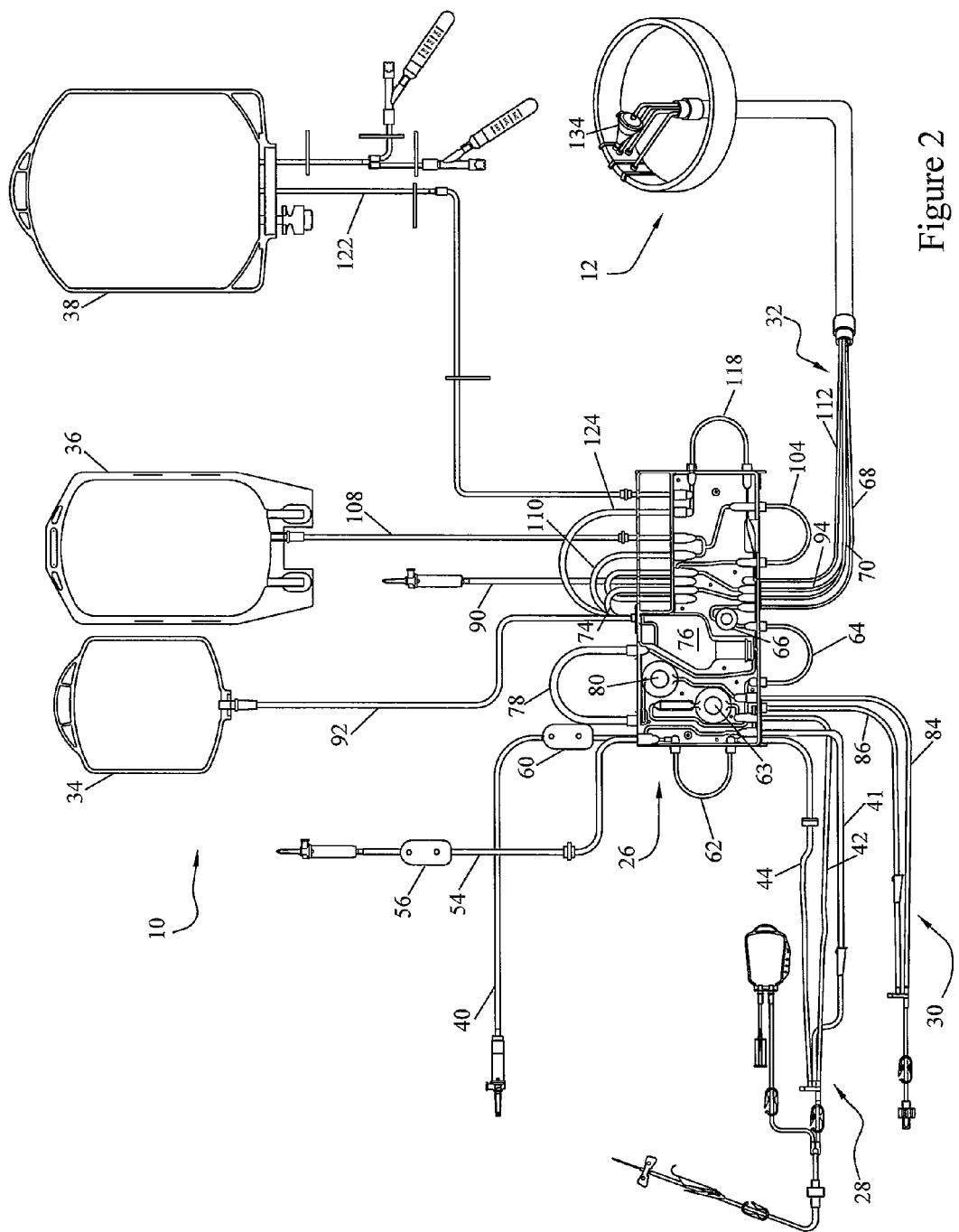
FIG. 2 illustrates a tubing and bag set including an extracorporeal tubing circuit, a cassette assembly, and collection bag assembly for use in or with the system of FIG. 1 pursuant to the present invention.

An extracorporeal tubing circuit 10, shown in FIG. 2, may include a cassette 26 and a number of tubing/collection assemblies 28, 30, 32, 34, 36, 38 and 40. A blood removal tubing assembly 28 provides a needle interface for withdrawing blood from a donor to the remainder of the tubing circuit 10. A blood return tubing assembly 30 provides a needle interface for returning blood components and other fluids to the donor. A single needle interface may also be used. Three lines 41, 42, 44 are provided in blood removal tubing assembly 28 (see FIG. 3) for removal of blood from the donor. A cassette 26 is connected between the tubing assembly 28, which connects to the donor, and blood inlet/blood component tubing line sub-assembly 32, which provides the interface between cassette 26 and blood processing vessel 12. The cassette 26 orients tubing segments in predetermined spaced relationships within the cassette 26 for ultimate engagement with valve members on apheresis device 6. Such valves will, when activated, control flow through loops and tubing.

Four lines 68, 70, 94 and 112 are shown in FIG. 2 for transport of blood and components to and from the processing vessel 12. An anticoagulant tubing assembly 40, a vent bag 34, a plasma collection assembly 36, and a white blood cell collection bag 38 are also interconnected with cassette 26.

The extracorporeal tubing circuit 10 and blood processing vessel 12 are pre-connected to form a closed, sterilized, disposable assembly for a single use.

When the tubing circuit 10 has been mounted on the blood component separation device 6, saline solution primes the tubing circuit through a saline line 54 and filter 56 (see FIG. 2). Saline flows through an internal passageway in the cassette 26 and through the line 41 to the distal end of the blood removal assembly 28. Saline can then flow up a blood withdrawal line 42 into the other tubes and passageways of the circuit 10 and up an anticoagulant line 44 in preparation for blood processing. A supply or bag (not shown) of anticoagulant connects to a distal end of the anticoagulant tubing assembly 40. Anticoagulant solution flows past a filter 60 and a first pump loop 62 through the anticoagulant line 44 to the distal end of the blood removal assembly. The pump loop 62 and other pump loops described herein couple with peristaltic pumps on the blood processing device 6 in a known manner. The device 6 controls the direction and rate of flow of the fluids described herein by controlling the speed and direction of the peristaltic pumps and the position of various valves.

The blood removal line 42 conducts blood into the cassette 26, where the blood passes a first pressure sensor 63 and a second pump loop 64. A second pressure sensor 66, between second pump loop 64 with its associated pump and blood inflow line 68 to the blood processing vessel 12, senses the fluid pressure effective at an inlet to the blood processing vessel 12. Emanating from blood processing vessel 12 is an RBC outlet tubing line 70 of the blood inlet/blood component tubing assembly 32. The outlet tubing line 70 connects to an external loop 74 to a return reservoir 76. The return reservoir 76 contacts sensors on the device 6 that detect low and high fluid levels. The device 6 keeps the fluid in the reservoir between these two levels by controlling flow out of the reservoir past a return pump loop 78 and a return pressure sensor 80. As the fluid level in the reservoir 76 is constantly rising and falling, a vent bag 34 connects to the reservoir 76 through a vent tube 92. Air can flow between the reservoir 76 and the vent bag 34 in a sterile manner. Fluid flows into a return tube 84 in the blood return assembly 30. The return assembly 30 also comprises a saline line 86 connected internally in the cassette 26 to saline line 54 for priming as described above. If desired, red blood cells could be withdrawn through the replacement line 90 and collected in a collection bag (not shown).

Plasma may also be collected from the blood processing vessel 12 into plasma bag 36. When desired, plasma is withdrawn from the blood processing vessel 12 through plasma line 94 to a pump loop 104. A valve (not shown) diverts the plasma either into a collect tube 108 to the plasma bag 36, or into a connecting loop 110 to the reservoir 76. Excess plasma in the reservoir 76 is returned to the donor in the same way as red blood cells, as described above.

White blood cells flow out of the blood processing vessel 12 through a fourth cell line 112 in the tubing line sub-assembly 32. In the cassette 26, a red-green photo sensor (not shown) may be used to control periodic flushing of white blood cells out of the blood processing vessel 12 into the collect bag 38. The white blood cells flow through a pump loop 118, which engages a peristaltic pump on the separation device 6. The pump loop 118 connects to a valved passageway in the cassette 26. The blood processing device 6 can control a valve to direct white blood cells either into a collect tube 122 and thence into the collect bag 38, or into a connection loop 124 and thence into the reservoir 76. Excess white blood cells in the reservoir 76 may be returned to the donor in the same way as red blood cells and plasma, as described above.

During a blood removal, whole blood will be passed from a donor into tubing line 42 of blood removal tubing assembly 28. The blood is pumped by the device 6 via pump loop 64, to the blood processing vessel 12 via the cassette 26 and line 68 of the blood inlet/blood component tubing assembly 32. Separation processing then occurs on a substantially continuous basis in the blood processing vessel 12, i.e., blood flows substantially continuously therein, is continuously separated and flows as separated components therefrom. After separation processing in vessel 12 (though separation is continuously occurring), uncollected blood components are transferred from the processing vessel 12 to and through cassette 26, into reservoir 76 of cassette 26 up to a predetermined level. The blood component separation device 6 may initiate a blood return submode wherein components may be returned to the donor through return line 84. The cycle between blood removal and blood return submodes will continue until a predetermined amount of blood components have been harvested. In an alternative single needle scheme, as is known in the art, blood may be alternately removed from the donor and returned to a donor through a single needle.

A bracket (not shown) is provided on a top surface of the centrifuge assembly 16. The bracket releasably holds an LRS or cell separation chamber 134 on the centrifuge assembly 16 so that an outlet 136 of the cell separation chamber 134 is positioned closer to the axis of rotation than an inlet 138 of the chamber 134. The bracket orients the chamber 134 on the centrifuge assembly 16 with a longitudinal axis of the cell separation chamber 134 in a plane transverse to the rotor's axis of rotation. In addition, the bracket is arranged to hold the cell separation chamber 134 on the centrifuge assembly 16 with the cell separation chamber outlet 136 facing the axis of rotation. Although the chamber 134 is preferably on a top surface of the centrifuge assembly 16, the chamber 134 could also be secured to the centrifuge assembly 16 at alternate locations, such as beneath the top surface of the centrifuge assembly 16.

Figure 3:
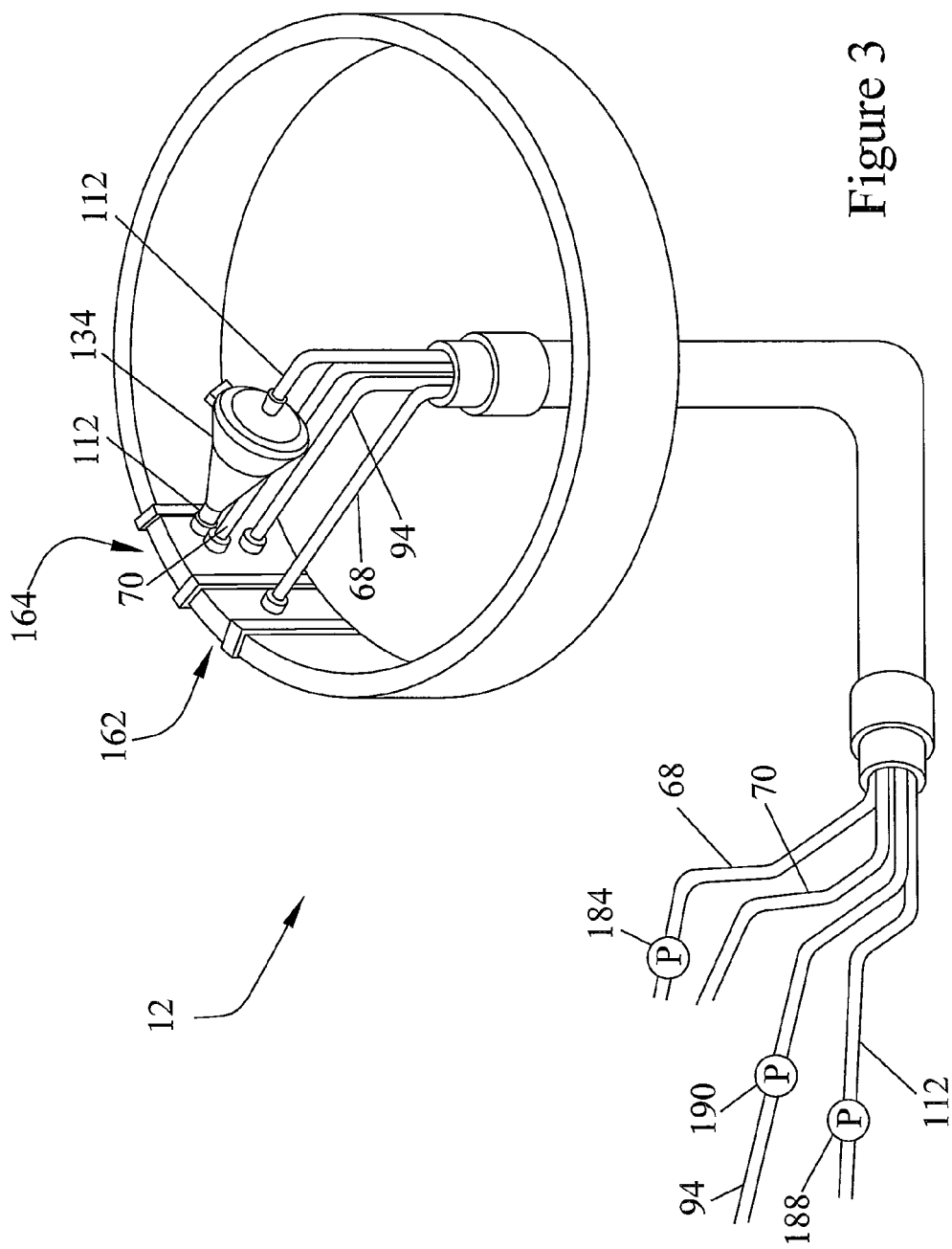
FIG. 3 is a perspective view of a blood processing vessel and the cell separation chamber.
Figure 5:
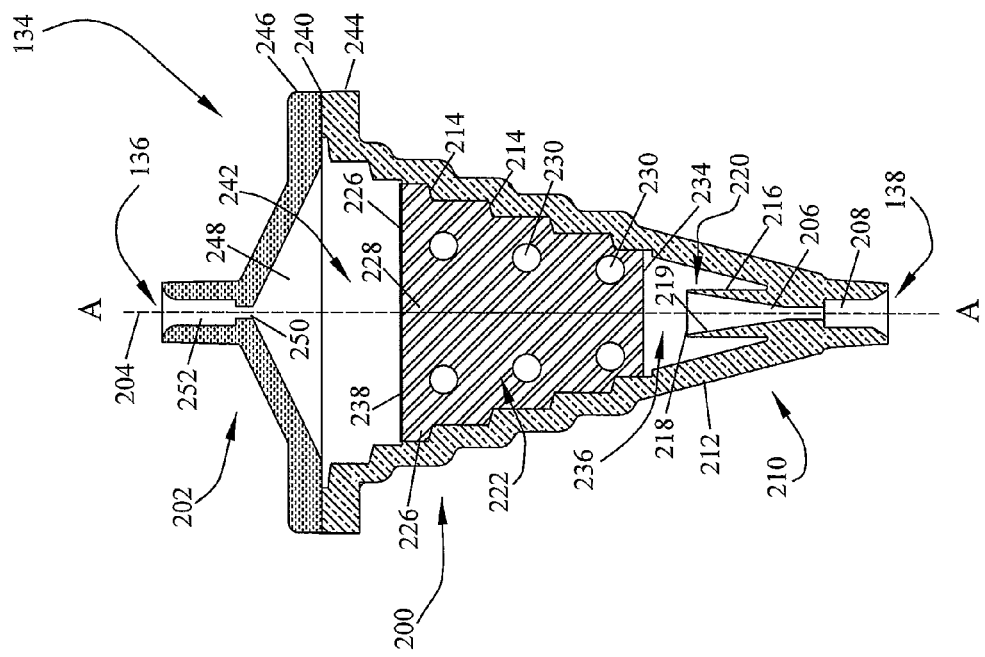
FIG. 5 is a cross-sectional view of the cell separation chamber of FIG. 4, taken along line 5-5.
Figure 4:
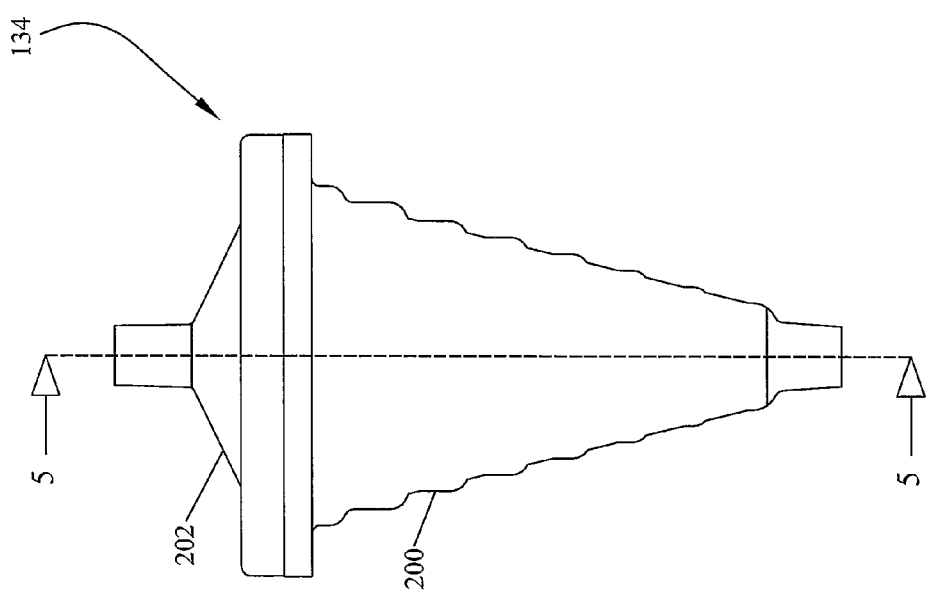
FIG. 4 is a plan view of the cell separation chamber of FIG. 3.
Figure 7:
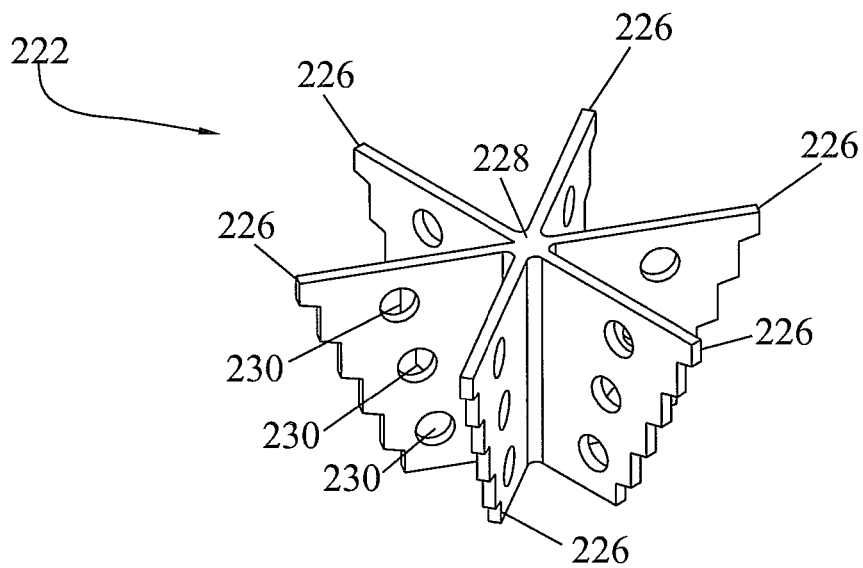
FIG. 7 is a perspective view of a baffle for use in the cell separation chamber.
Figure 6:
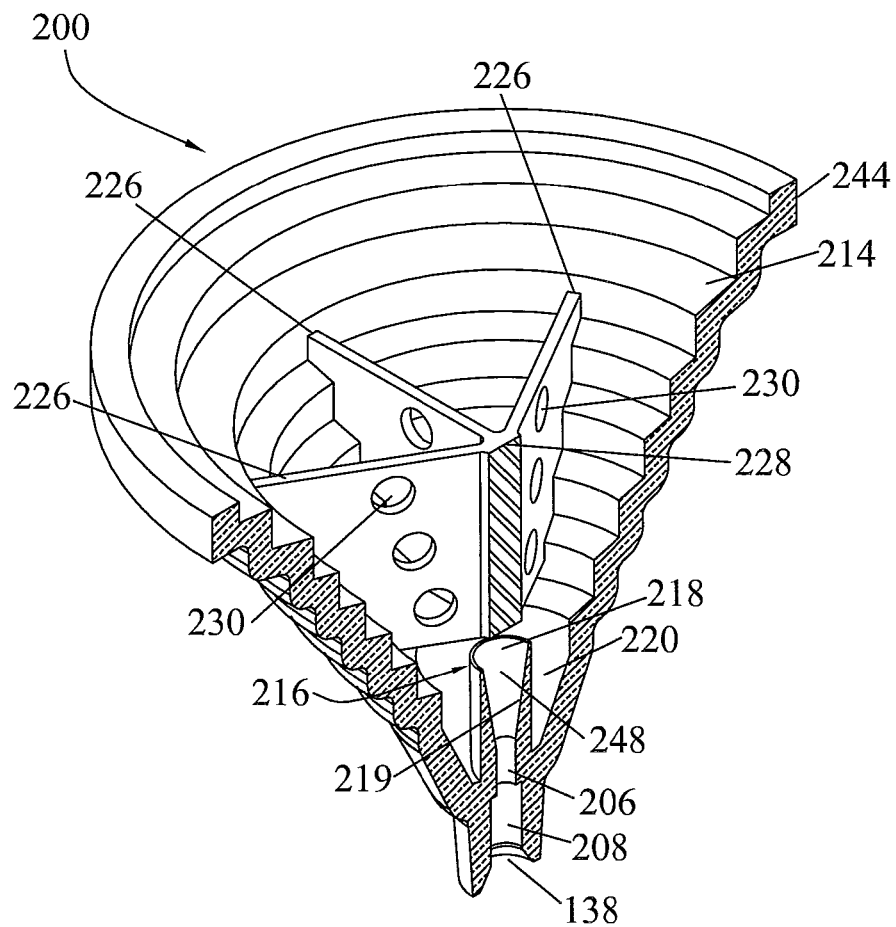
FIG. 6 is a perspective cross-section of a bottom portion of the cell separation chamber of FIG. 4.

FIG. 3 schematically illustrates a portion of the blood processing vessel 12 and cell separation chamber 134. The blood processing vessel 12 has a generally annular flow path and includes an inlet portion 162 and outlet portion 164.

The inlet portion 162 includes an inflow tube 68 for conveying a fluid to be separated, such as whole blood, into the processing vessel 12. During a separation procedure, substances entering the inlet portion 162 flow around the vessel 12 and stratify according to differences in density in response to rotation of the centrifuge assembly 16. The outlet portion 164 includes outlets for the RBC line 70, the plasma line 94, and cell line 112 for removing separated substances from the separation vessel 12. Each of the components separated in the vessel 12 is collected and removed in only one area of the vessel 12, namely the outlet portion 164.

The outlet of the cell line 112 is connected to the cell separation chamber inlet 138 to pass the intermediate density components, including white blood cells, into the cell separation chamber 134. Components initially separated in the separation vessel 12 are further separated in the cell separation chamber 134. For example, white blood cells could be separated from plasma and platelets in the cell separation chamber 134. This further separation takes place by forming a saturated fluidized bed of particles, such as white blood cells, in the cell separation chamber 134. As schematically shown in FIG. 3, a plurality of pumps 184, 188, and 190 are provided for adding and removing substances to and from the blood processing vessel 12 and cell separation chamber 134.

An inflow pump 184 is coupled to the inflow line 68 to supply the substance to be separated, such as whole blood, to the inlet portion 162. In addition, a first collection pump 188 is coupled to the cell line 112 connected to the cell separation chamber outlet, and a second collection pump 190 is coupled to the plasma collection line 94. The first collection pump 188 draws liquid and particles from the cell separation chamber outlet 136 and causes liquid and particles to enter the cell separation chamber 134 via the cell separation chamber inlet 138. The second collection pump 190, on the other hand, removes primarily low-density substances from the separation vessel 12 via the plasma line 94. The pumps 184, 188, and 190 are peristaltic pumps, which prevent significant damage to blood components. The pumps 184, 188, and 190 control the flow rate of substances flowing to and from the blood processing vessel 12 and the cell separation chamber 134. A saturated fluidized bed of particles is maintained within the cell separation chamber 134 to cause other particles to be retained in the cell separation chamber 134.

Blood within the processing vessel 12 is subjected to centrifugal force causing components of the blood components to separate. The components of whole blood stratify in order of decreasing density as follows: (1) red blood cells, (2) white blood cells, (3) platelets, and (4) plasma. The controller regulates the rotational speed of the centrifuge channel assembly 16 to ensure that this particle stratification takes place. A layer of red blood cells (high density components) forms along the outer wall of the processing vessel 12 and a layer of plasma (lower density components) forms along the inner wall of the processing vessel 12. Between these two layers, the intermediate density platelets and white blood cells (intermediate density components) form a buffy coat layer.

In the outlet portion 164, platelet-poor plasma flows through the line 94. These relatively low-density substances are pumped by the collection pump 190 through the plasma collection line 94. Red blood cells are removed via the RBC line 70. The red blood cells flow through the RBC line 70 and can then be returned to the donor or, alternatively, collected and optionally recombined with other blood components or further separated. Accumulated white blood cells are removed from the channel via the cell line 112, along with platelets and plasma. As the platelets, plasma, white blood cells, and possibly a small number of red blood cells pass through the line 112, these components flow into the cell collection chamber 134, so that a saturated fluidized particle bed may be formed.

In addition, the pump 188 conveys at least the plasma, platelets, and white blood cells at a predetermined flow rate through the cell collection line 112 and into the inlet 138 of the cell separation chamber 134. When the platelet and white blood cell particles enter the cell separation chamber 134, they are subjected to two opposing forces. Plasma flowing through the cell separation chamber 134 with the aid of pump 188 establishes a first viscous drag force when plasma flowing through the cell separation chamber 134 urges the particles toward the outlet 136. A second centrifugal force created by rotation of the channel assembly 16 and cell separation chamber 134 acts to urge the particles toward the inlet 138. The rotational speed of the centrifuge assembly 16 and the flow rate of the pump 188 causes platelets and white blood cells to collect in the cell separation chamber 134. As plasma flows through the cell separation chamber 134, the flow velocity of the plasma decreases and reaches a minimum as the plasma flow approaches the maximum cross-sectional area of the cell separation chamber 134. The white blood cells accumulate somewhat radially outward from the maximum cross-sectional area of the chamber 134.

The cell separation chamber is shown in detail in FIGS. 4, 5, 6 and 7. The cell separation chamber 134 may be constructed in two pieces, a main body 200 and a cap 202, both being symmetrical around an axis 204. The main body 200 has an inlet 138 comprising a through bore 206 and a concentric stopped bore 208. The diameter of the through bore 206 corresponds to the inside diameter of the cell line 112, while the diameter of the stopped bore 208 corresponds to the outside diameter of the line 112, so that the cell line 112 can be seated in the stopped bore 208 and a fluid passageway of constant diameter can be formed between the line 112 and the through bore 206. The through bore 206 opens into a frustro-conical segment 210. A wall 212 of the first frustro-conical segment 210 comprises a plurality of steps 214 which generally taper away from the axis 204. The through bore 206 rises into the frustro-conical segment 210 through a protruding inlet 216. A mouth 218 of the protruding inlet 216 opens into the frustro-conical segment 210 spaced away from the wall 212, thereby forming a circumferential well 220 between the wall and the protruding inlet. A stream of fluid leaving the protruding inlet and entering the chamber is insulated from the effects of the wall 220 by a relatively static fluid layer. The stream is therefore less likely to adopt a flow path along the wall, under the influence of Coriolis forces, but rather will remain in the center of the chamber, allowing more uniform mixing of cells and other particles within the chamber. An inner surface 219 of the protruding inlet flares slightly outwardly towards the mouth 218 of the protruding inlet 216. This reduces the flow velocity of fluid passing through the protruding inlet and lessens Coriolis effects as the fluid enters the chamber.

A baffle 222 within the chamber 210 inhibits laminar mixing in the chamber. The baffle comprises a plurality of vanes 226, for example, six vanes extending radially outward from a center 228 at equal angles. Each vane is pierced by openings such as holes 230 or slots 232 (FIG. 9), which allow limited circumferential circulation in the areas between adjacent vanes. If injection molding is used to manufacture the baffle, it is generally easier to mold the baffle with slots, rather than holes. A bottom edge 234 of the baffle is spaced away from the mouth 218 of the protruding inlet 216, forming a plenum 236 where the fluid and suspended particle entering the chamber can form a uniform mixture before being constrained by the baffle. Similarly, an upper edge 238 of the baffle is spaced away from a junction 240 between the cap 202 and the main body 200, forming a second plenum 242 above the baffle where fluid and particles slow down and mix uniformly.

In the illustrated embodiment, the main body 200 of the cell separation chamber 134 further comprises a circumferential flange 244, which is supported in the holder. The cap 202 comprises a rim 246 that fits against the flange 244. An interlocking groove and ridge (not shown) may be provided between the rim 246 and flange 244 for sealing, if desired. The cap 202 and main body 200 may be joined by ultrasonic welding or other suitable techniques as known in the art. The cap opens into an abrupt frustro-conical segment 248. The abrupt segment 248 tapers towards the axis 204. The abrupt segment 248 funnels filtered blood components into the outlet 136 without excessive turbulence or damage to the blood components. The outlet 136 comprises a through bore 250 and a concentric stopped bore 252. The diameter of the through bore 250 corresponds to the inside diameter of the cell line 112, while the diameter of the stopped bore 252 corresponds to the outside diameter of the cell line 112, so that the line 112 can be seated in the stopped bore 252 and a fluid passageway of constant diameter can be formed between the line 112 and the through bore 250. The through bore 250 opens into the frustro-conical segment 248.

The cell separation chamber 134 described above is particularly effective for filtering white blood cells from platelets, to produce collected platelet products that are highly leuko-reduced that is, free from white blood cells.

A second embodiment is illustrated in FIG. 8 and FIG. 9. Parts that the two embodiments have in common have the same numbers and functions as described above. This second embodiment differs primarily in features related to a main body 200a. In the main body 200a of the second embodiment, an initial separation chamber 260 captures many of the white blood cells. The initial separation chamber is frustro-conical and receives fluid from the inlet 138 near a narrow end 262 of the chamber 260. Filtered biologic fluid leaves the initial separation chamber at a wide end 264 and enters a pipe 266 by way of a funnel segment 268. The pipe 266 communicates with the protruding inlet 216a, as described above. A radial wall 267 provides structural stability in the region of the pipe 266. A solid body around the pipe 266 is possible, but less desirable because of unpredictable distortions that might occur as the plastic material used to form the main body 200a cools.

Residual white blood cells are captured in the second separation chamber 270, which has a well 220, baffle 222, clear spaces 236, 242, and other features as described above. In addition, a recirculation channel 272 conducts fluid and particles from the bottom of the well 220 into the pipe 266. A few cells, such as white cells, platelets, or occasional red blood cells, may collect in the bottom of the well 220. These cells are drawn out of the well through the recirculation channel and returned to the pipe 266 or through bore. The addition of these re-circulated cells to the stream passing into the separation chamber 270 raises the average rate of cells leaving the protruding inlet 216a. This tends to reduce the relative variation in the rate of cells leaving the protruding inlet. This implies that the flow characteristics will be relatively more uniform and there will be less likelihood of disturbing the equilibrium of the fluidized bed being developed in the separation chamber 270 by an unusually large number of cells entering the chamber in a particular period of time. It is believed that this negative feedback phenomenon will contribute to more stable processing.

It is also desirable to return as many white cells as possible to the donor at the end of a platelet collection procedure. During the procedure, white cells that settle into the well can be drawn back into the fluid flow and suspended in the second chamber 270. This is thought to contribute to the viability of the white cells. At the end of a procedure, cells remaining in the tubing circuit 10 are returned to the donor by back flushing saline or plasma through the elutriation chamber 134, the blood processing vessel 12 and other parts of the extracorporeal tubing circuit 10. Some cells that might otherwise be retained in the well 220 are flushed through the recirculation channel 272 to be returned to the donor.

The second embodiment shown in FIG. 8 and FIG. 9 is illustrated in prototype form. It will be understood by those skilled in the art that for manufacturing purposes the main body may be molded in different forms or in multiple parts without departing from the teachings of this invention. For example the main body might be comprised of two symmetrical injection molded parts, each part being symmetrical about a plane bifurcating the recirculation channel 272, pipe 266, and separation chambers 260, 270. In addition, the wall 267 surrounding the pipe 266 could be replaced with a plurality of radial fins to provide the same structural integrity, but allowing for a mold design suitable for manufacturing. Design of molds for manufacturing is within the scope of one skilled in the art, in view of the disclosure given herein.

The elutriation chamber described herein both filters white blood cells from a separated blood component comprising plasma, platelets and white blood cells and suspends the white cells within the elutriation chamber for return to the donor. The flow of fluid into the chamber is separated from the chamber walls by the protruding inlet that extends into the chamber. Laminar mixing is restrained by the vanes of the baffle. In addition, a recirculation channel may normalize particle flow rate into the chamber and may return white blood cells to suspension within the chamber or to the donor, according to the steps of the blood collection procedure. Successive chambers may provide staged filtration of the white blood cells from the blood components passing through the elutriation apparatus.

Although the inventive device and method have been described in terms of filtering white blood cells, this description is not to be construed as a limitation on the scope of the invention. It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A disposable blood separation set comprising
   a blood processing chamber adapted to be mounted on a rotor of a centrifuge;
   a rigid, generally frustro-conical cell separation chamber having a center axis in fluid communication with said processing chamber;
   the cell separation chamber having an inlet and an outlet and an inner wall defining a separation area within said cell separation chamber, said inlet being connected to said blood processing chamber, and
   a plurality of planar vanes, radially symmetrically aligned around said axis of said cell separation chamber within said separation area in said cell separation chamber, each vane comprising said axis of said separation chamber and extending radially outwardly therefrom, said plurality of vanes intersecting at said axis.

2. The disposable blood separation set of claim 1 wherein the vanes are thin walls.

3. The disposable blood separation set of claim 1 wherein said vanes have openings therein.

4. The disposable blood separation set of claim 3 wherein said openings comprise holes.

5. The disposable blood separation set of claim 3 wherein said openings comprise slots.

6. The disposable blood separation set of claim 1 wherein said vanes have a bottom edge, said bottom edge being spaced away from said inlet.

7. The disposable blood separation set of claim 6 wherein said inlet comprises a protruding inlet.

8. The disposable blood separation set of claim 1 wherein said vanes have an upper edge, said upper edge being spaced away from said outlet.

9. The disposable blood separation set of claim 8 wherein said cell separation chamber has a major diameter and said upper edge of said vanes stop short of said major diameter thereby providing a flow-equalizing volume.

10. The disposable blood separation set of claim 9 wherein said cell separation chamber comprises an exit cone adjacent said outlet and wherein said flow-equalizing volume is prior to said exit cone.

* * * * *